United States Patent
Harders

(10) Patent No.: US 10,022,261 B1
(45) Date of Patent: Jul. 17, 2018

(54) INCONTINENCE DEVICE WITH ATMOSPHERIC EQUILIBRIUM VALVE ASSEMBLY

(71) Applicant: BioDerm, Inc., Largo, FL (US)

(72) Inventor: James Alan Harders, Indian Rocks Beach, FL (US)

(73) Assignee: BioDerm, Inc., Largo, FL (US)

( * ) Notice: Subject to any disclaimer, the term of this patent is extended or adjusted under 35 U.S.C. 154(b) by 0 days.

(21) Appl. No.: 15/680,335

(22) Filed: Aug. 18, 2017

Related U.S. Application Data

(60) Provisional application No. 62/513,367, filed on May 31, 2017.

(51) Int. Cl.
| | |
|---|---|
| *E03C 1/10* | (2006.01) |
| *F16K 24/00* | (2006.01) |
| *A61F 5/44* | (2006.01) |
| *A61F 5/453* | (2006.01) |

(52) U.S. Cl.
CPC ............ *A61F 5/4405* (2013.01); *A61F 5/453* (2013.01); *Y10T 137/3331* (2015.04); *Y10T 137/788* (2015.04); *Y10T 137/7884* (2015.04); *Y10T 137/7885* (2015.04); *Y10T 137/7888* (2015.04)

(58) Field of Classification Search
CPC .. A61F 5/4405; A61F 5/453; Y10T 137/3331; Y10T 37/788; Y10T 137/7885; Y10T 137/7884; Y10T 137/7888
See application file for complete search history.

(56) References Cited

U.S. PATENT DOCUMENTS 2,371,449 A  *  3/1945  Langdon ................... E03F 7/04
                                                    137/526
2,875,758 A      3/1959  Fuzak et al.
(Continued)

FOREIGN PATENT DOCUMENTS

| GB | 2197849 A1 | 6/1988 |
| GB | 2197849 B1 | 7/1991 |

(Continued)

OTHER PUBLICATIONS

Cook, Inc., Non-Adhesive Silicone Condom Catheter, Product Catalog, Jan. 2012, pp. 2-4, Bloomington, Indiana, U.S.A.
(Continued)

*Primary Examiner* — Craig Schneider
*Assistant Examiner* — Kevin Barss
(74) *Attorney, Agent, or Firm* — Stephen E. Kelly; Hill Ward Henderson, P.A.

(57) ABSTRACT

A male external incontinence device comprising a drainage tube assembly having a proximal chamber in fluid communication with a drainage tube, the proximal chamber comprising an atmospheric equilibrium valve assembly. The atmospheric equilibrium valve assembly has an airway conduit with a upper portion in fluid communication with the proximal chamber, and a lower portion having an air inlet chamber. A one-way air valve disposed in the airway conduit above the air inlet chamber, the one-way air valve comprising a first pair of opposing walls disposed at a first set of opposing angles such that the first pair of opposing walls abut each other at an apex, the apex having a self-sealing slit.

20 Claims, 8 Drawing Sheets

(56) References Cited

U.S. PATENT DOCUMENTS

| | | | | |
|---|---|---|---|---|
| 2,883,985 A | * | 4/1959 | Evans | A61F 5/4405 |
| | | | | 128/DIG. 24 |
| 3,155,107 A | * | 11/1964 | Woodford | E03C 1/106 |
| | | | | 137/218 |
| 3,298,370 A | | 1/1967 | Beatty | |
| 3,312,221 A | * | 4/1967 | Overment | A61F 5/44 |
| | | | | 128/DIG. 24 |
| 3,598,124 A | | 8/1971 | Anderson | |
| 3,788,324 A | | 1/1974 | Lim | |
| 3,835,857 A | | 9/1974 | Rogers, III et al. | |
| 3,861,394 A | | 1/1975 | Villari | |
| 3,967,645 A | | 7/1976 | Gregory | |
| 3,968,925 A | * | 7/1976 | Johnston | A61F 5/4405 |
| | | | | 137/855 |
| 4,013,077 A | | 3/1977 | Ritota et al. | |
| 4,197,848 A | | 4/1980 | Garrett et al. | |
| 4,419,097 A | | 12/1983 | Rowland | |
| 4,449,971 A | | 5/1984 | Cawood | |
| 4,563,183 A | | 1/1986 | Barrodale et al. | |
| 4,581,763 A | * | 4/1986 | Olsen | A61F 5/44 |
| | | | | 383/44 |
| 4,626,250 A | | 12/1986 | Schneider | |
| 4,737,148 A | | 4/1988 | Blake | |
| 4,776,848 A | | 10/1988 | Solazzo | |
| 4,795,449 A | | 1/1989 | Schneider et al. | |
| 4,932,938 A | | 6/1990 | Goldberg et al. | |
| 5,078,707 A | | 1/1992 | Peter Klug | |
| 5,087,252 A | | 2/1992 | Denard | |
| 5,207,652 A | | 5/1993 | Kay | |
| 5,263,946 A | | 11/1993 | Klug | |
| 5,263,947 A | | 11/1993 | Kay | |
| 5,267,989 A | | 12/1993 | Moyet-Ortiz | |
| 5,380,312 A | | 1/1995 | Goulter | |
| 5,409,474 A | | 4/1995 | Fleeman-Hardwick | |
| 5,417,664 A | | 5/1995 | Felix et al. | |
| 5,618,277 A | | 4/1997 | Goulter | |
| 5,643,235 A | | 7/1997 | Figuerido | |
| 5,683,354 A | | 11/1997 | Levy | |
| 5,713,880 A | | 2/1998 | Anderson | |
| 5,741,240 A | | 4/1998 | Olsen | |
| 5,797,890 A | | 8/1998 | Goulter et al. | |
| 5,827,247 A | | 10/1998 | Kay | |
| 5,830,932 A | | 11/1998 | Kay | |
| 5,935,091 A | | 8/1999 | Friedman | |
| 6,045,542 A | * | 4/2000 | Cawood | A61F 5/4405 |
| | | | | 604/327 |
| 6,113,582 A | | 9/2000 | Dwork | |
| 6,179,818 B1 | | 1/2001 | Kydonieus et al. | |
| 6,223,751 B1 | | 5/2001 | Park | |
| 6,296,627 B1 | | 10/2001 | Edward | |
| 6,632,204 B2 | | 10/2003 | Guldfeldt et al. | |
| 6,679,867 B2 | | 1/2004 | Miskie | |
| 6,793,651 B1 | * | 9/2004 | Bennett | A61F 5/4405 |
| | | | | 604/328 |
| 7,147,625 B2 | | 12/2006 | Sarangapani et al. | |
| 7,608,067 B2 | | 10/2009 | Bonni | |
| 7,896,857 B2 | * | 3/2011 | Kay | A61F 5/4408 |
| | | | | 4/144.1 |
| 8,485,398 B2 | * | 7/2013 | Kneer | B65D 47/18 |
| | | | | 137/852 |
| 8,551,062 B2 | * | 10/2013 | Kay | A61F 5/453 |
| | | | | 604/180 |
| 2001/0005782 A1 | | 6/2001 | Tanghoj et al. | |
| 2002/0026163 A1 | | 2/2002 | Grundke | |
| 2003/0149408 A1 | | 8/2003 | Levinson | |
| 2004/0034335 A1 | | 2/2004 | Dolan | |
| 2006/0079854 A1 | | 4/2006 | Kay et al. | |
| 2006/0122568 A1 | | 6/2006 | Elson et al. | |
| 2007/0117880 A1 | | 5/2007 | Elson et al. | |
| 2007/0161949 A1 | | 7/2007 | Knox et al. | |
| 2008/0183157 A1 | | 7/2008 | Walters | |
| 2010/0286667 A1 | | 11/2010 | Paz | |
| 2013/0213415 A1 | | 8/2013 | Kay et al. | |
| 2014/0214008 A1 | | 7/2014 | Babb et al. | |

FOREIGN PATENT DOCUMENTS

| | | |
|---|---|---|
| WO | 9936009 A1 | 7/1999 |
| WO | 2006044249 A2 | 4/2006 |

OTHER PUBLICATIONS

Cook, Inc., VPI Non-Adhesive Silicone Condom Catheter, Technical Drawing, Aug. 30, 1996, Bloomington, Indiana, U.S.A.

* cited by examiner

INCONTINENCE DEVICE WITH ATMOSPHERIC EQUILIBRIUM VALVE ASSEMBLY

CROSS-REFERENCE TO RELATED APPLICATION

Pursuant to 35 U.S.C. § 119(e), this application claims the benefit of U.S. Provisional Patent Application Ser. No. 62/513,367, filed on May 31, 2017, the entire contents of which are incorporated herein by this reference.

BACKGROUND

(1) Field of Endeavor

The device disclosed herein relates generally to the field of incontinence devices, and more particularly to an external incontinence device adapted for attachment between the waist and knee of the user.

(2) Description of Related Art

Urinary incontinence is a common medical problem in older males, and it sometimes occurs in juveniles in the form of nocturnal enuresis. Those experiencing these maladies can benefit from the use of an external catheter that can be worn on the body and thus be transported with the user throughout normal activities. Such devices also can be worn during normal sleep patterns.

Many such devices carry the risk of unwanted side effects, such as skin maceration, skin irritation, or microbial skin infiltration including associated infections with these skin related traumas. Also common are urinary tract infections associated with conventional urinary catheters and other incontinence devices, such as condom catheters and adult or juvenile absorbent pads.

There are several other adverse side effects common with current treatment for urinary incontinence, most prominent of which is a high incidence of infections associated with indwelling catheters. In many instances, urinary tract infections are proximally caused by the constant contact of exposed penis tissue to the urine collected in a tube, reservoir, or pad. Incontinence pads or diapers also have been known to contribute to infections because the excreted urine in these devices is conducive to bacterial growth.

Other issues like skin maceration or the presence of granuloma occurs not only when the skin is exposed to water from external sources, but also when moisture is trapped against the skin surface. This is the case with condom catheters and diapers urinary incontinence products. Granuloma appears when sloughed skin is trapped in the lining of the diaper in the sheath of the condom and then collects on the diaper pad or in the sheath of the condom. This granuloma may then migrate to other sensitive areas of the body thus initiating a nosocomial secondary or tertiary infection that will require a treatment regimen not associated with the primary reason for the hospital visit.

In addition to the medical related issues associated with the previous art, there are other problems associated with devices that incorporate a urine collection chamber, if the chamber is disposed distant from the urine collection device. One such problem, defined herein as the urine backup phenomenon, which occurs when urine backs up or fails to drain from the urinary drainage tubing. As a consequence, urine reflux can occur, and this urine can return through the urinary drainage tubing, or catheter, and into contact with the user. Users with indwelling catheters can incur bladder infections as previously stated.

An additional problem related to backflow of urine is generated when the urine collection chamber is positioned adjacent to the abdominal area. In this regard a user wearing an external urine collection device may experience backflow of urine from the abdominal urine collection chamber and from the chamber's proximal urinary drainage tubing into the external device due to the effects of gravity and periodic variations of intra-abdominal and bladder pressure.

Another issue, sometimes called a siphon effect, refers to a barometric phenomenon whereby negative pressure accumulates in the urinary drainage tubing and urine collection chamber of a conventional urine collection assembly. The siphon effect phenomenon occurs as urine descends through the relatively long lengths of urinary drainage tubing present in known urine collection assemblies that directs urine from the urine collection device to the urine collection chamber. As urine descends through the urinary drainage tubing and drops into the urine collection chamber, which can be up to 42 inches (106.68 cm) in length, below the user's penis. In this configuration, negative intra-luminal pressure accumulates behind the column of urine causes a partial vacuum within the tube lumen. When long drainage tubing is employed in an external catheter system, the vacuum created is most prevalent. Even a small vacuum pressure can cause discomfort to the user by drawing the tip of the glans into the main drainage tubing to which the long drainage tube is attached. This siphoning effect not rally occurs only when a user fully evacuates into the integral collection chamber assembly, or main drainage tubing, that is attached to long drainage tubing.

Thus there is a need in the medical art for an external incontinence device which is not invasive, does not promote harm such as initiating urinary tract infections, does not retain urine or other fluids in close proximity to the genital skin surface, is discreet when worn, may be used by males of all ages, promotes the user compliance and thus promotes an increase in the quality of life of the user.

SUMMARY

In one embodiment, the incontinence device comprises a drainage tube assembly having a drainage tube with an atmospheric equilibrium valve assembly. The integrated atmospheric equalization valve assembly mitigates the siphoning effect by allowing air into the drainage tube assembly, thereby increasing the positive air in the system overcoming the negative pressure that may be present in the drainage tube assembly. The atmospheric equilibrium valve comprises an airway conduit disposed in fluid communication with the drainage tube, and a lower portion having an air inlet chamber. A one-way air valve is disposed in the airway conduit above the air inlet chamber.

The one-way air valve comprises a first pair of opposing walls disposed at a first set of opposing angles such that the first pair of opposing walls abut each other at an apex. The apex comprises a self-sealing slit.

It is preferred, but not required, that the one-way air valve further comprises a second pair of opposing walls disposed at a second set of opposing angles. Each wall of the second pair of opposing walls spans between the first pair of opposing walls.

In another embodiment, the drainage tube assembly further comprises a proximal chamber in fluid communication with a drainage tube. The airway conduit is placed in fluid communication with the proximal chamber.

In any of the foregoing embodiments of the drainage tube assembly, the atmospheric equilibrium valve comprises amorphous material that is about 65 Shore A durometer material. It is preferred, but not required, that the thickness each of the walls of the atmospheric equalization valve is about 0.010 inch to about 0.020 inch.

The drainage tube assembly described herein is intended for attachment to an external incontinence device having a top para-meatal/stomal flexible hydrocolloid adhesive seal which is designed with a leaf pattern intended for attachment to the glans of the penis. Exemplary external incontinence devices suitable for use with the present drainage tube assembly are disclosed in U.S. Pat. No. 7,896,857 and U.S. Pat. No. 8,551,062.

More particularly, in one embodiment of a suitable external incontinence device, the top para-meatal/stomal flexible hydrocolloid adhesive seal is attached via a flexible UV curable adhesive to a housing or flexible polymer tube. Next there is a second flexible hydrocolloid seal that is attached to the side of the flexible polymer tubing to be at a fixed position relative to the first seal, and having a length to extend around the top para-meatal/stomal flexible hydrocolloid adhesive seal after the leaves are secured to the glans of the penis. The top para-meatal/stomal flexible hydrocolloid adhesive seal is designed with an aperture shaped to match the male penis meatus. This unique aperture may accommodate those end users/patients that have what is known as mild hypospadias. Hypospadias is normally a birth defect (congenital condition) in which the opening of the urethra is located inferior to the top of the glans. Additionally the top para-meatal/stomal flexible hydrocolloid adhesive seal accommodates physiological anomalies such as meatal erosion due to indwelling catheter wear.

In one embodiment, the top para-meatal/stomal flexible hydrocolloid adhesive seal is a highly elastic hydrocolloid wafer which has a unique leaf feature that is so designed as to eliminate or minimize the chance occurrence of a phenomenon called tenting of the overlapping leaves when attached to the glans of the penis. It also may accommodate a plethora of shapes and sizes of the penis glans, which aids in a positive seal around the glans so as to eliminate or minimize the chance occurrence of urine leakage during time of micturition by the patient. The top para-meatal/stomal flexible hydrocolloid adhesive seal wafer is designed with an anatomically friendly aperture to accommodate an end user/patient that may have the condition known as meatal erosion or a condition known as hypospadias. The soft and flexible nature of the hydrocolloid wafer offer additional comfort to the end user/patient during use. The second wafer is also a flexible highly elastic hydrocolloid material which will allow for attachment to the glans of the penis. This highly elastic hydrocolloid material will maintain its adhesion properties through all flaccid or erectile phases of the penis. The flexibly hydrocolloid wafer will form to the penis glans and not lose adhesion properties. Because of flexible nature and position of the device on the glans, this mitigates potential ischemia of the penis tissue.

In one embodiment, the drainage tube assembly disclosed herein further comprises a main flexible polymer drainage tube that is designed with a self-sealing, anti-reflux valve, which is integrated at the end of the tubing, thus eliminating extra components used in the construction of earlier urine collection assemblies. This main anti-reflux valve is designed to be reactive to very small pressure changes. The material chosen for this design is subject to modulus of elasticity changes, in that small increases in temperature changes will have a significant effect on the flexibility of the valve walls such that the modulus of elasticity of a polymer can change by as much as a factor of 1,000 when the temperature is increased. In this case, when normal body temperature urine comes in contact with the valve walls of the self-sealing, anti-reflux valve, the walls will distend (bellows effect) such that mimicking the meatus of the penis occurs, and thus allowing a free flow of urine from the main flexible polymer tube and into the urine reservoir.

As cited earlier in this application, the main purpose of the self-sealing, anti-reflux valve integrated into the main collection tube is configured to prevent urine from backing up out of the collection chamber and onto the end user and coming in contact with the users' urethra and possible ingress into the bladder of an end user. When a small amount of pressure is exerted on the reservoir collection bag, this will conversely collapse the walls of the self-sealing, anti-reflux valve, thus closing the valve and eliminating or minimizing the chance occurrence of urine regurgitating back toward the end user. This reduces the possibly of urine colleting in the main flexible polymer tubing, which reduces the possibility of contact between urine to the meatus or glans of the penis during the use of this device.

DESCRIPTION OF THE PREFERRED EMBODIMENTS

With reference to the drawings, the incontinence device will now be described with regard for the best mode and the preferred embodiments. The embodiments disclosed herein are meant for illustration and not limitation of the invention. An ordinary practitioner will appreciate that it is possible to create many variations of the following embodiments without undue experimentation.

Figure 1:
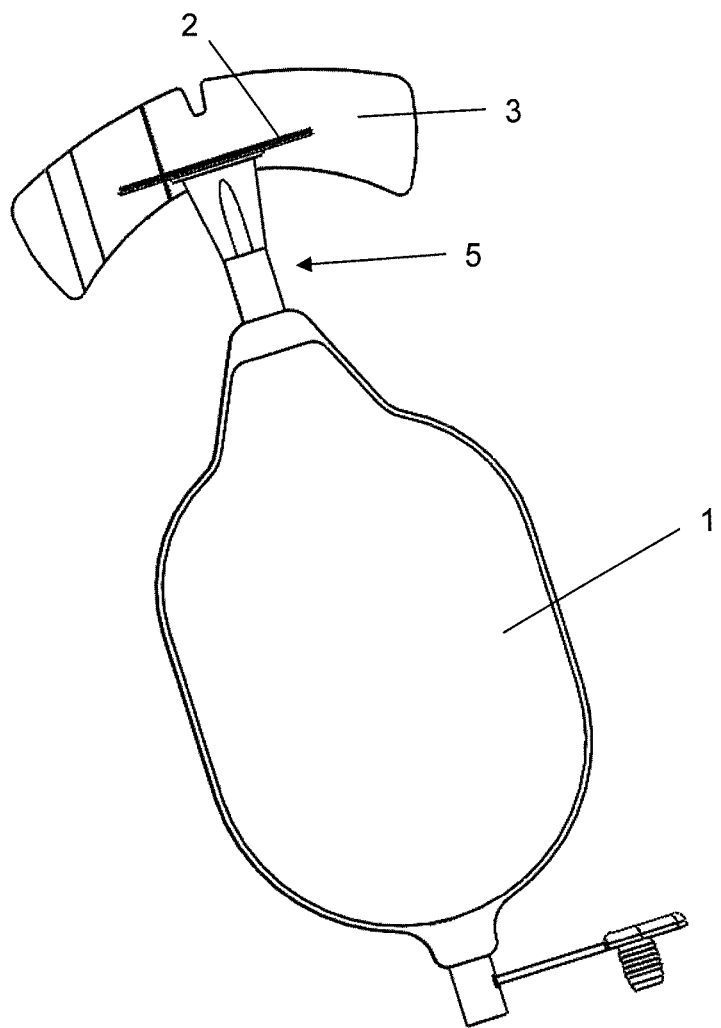
FIG. 1 shows one embodiment of a typical external incontinence device for which the present drainage tube assembly is intended for use.

In one embodiment, referring to FIG. 1, the drainage tube assembly 5 disclosed herein is primarily intended for use with an external incontinence device having a drainage bag 1 a parameatal barrier body 2, and an independent second seal 3. The parameatal barrier body 2 and an independent second seal 3 are attached to the user's body, and the present drainage tube assembly 5 provides drainage of urine into the drainage bag 1.

Figure 2:
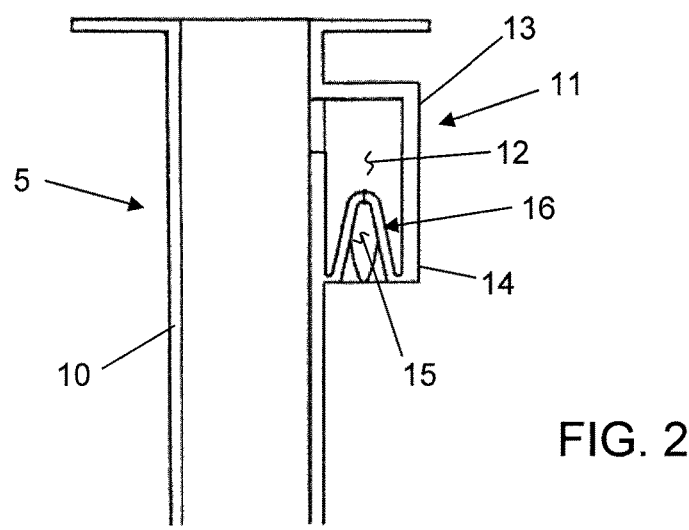
FIG. 2 is a cross sectional view of one embodiment of the present drainage tube assembly.
Figure 3:
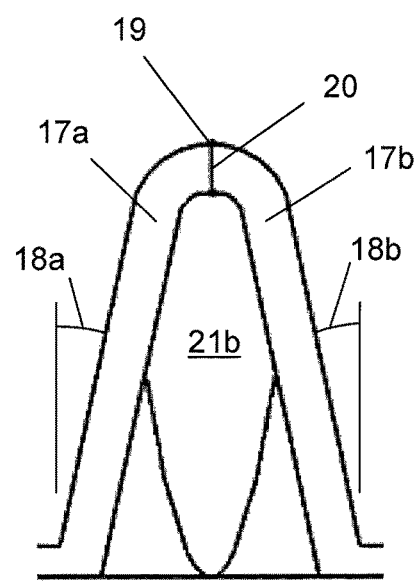
FIG. 3 is a cross sectional view of one embodiment of a one-way air valve, showing the first pair of opposing sidewalls in cross section.
Figure 4:
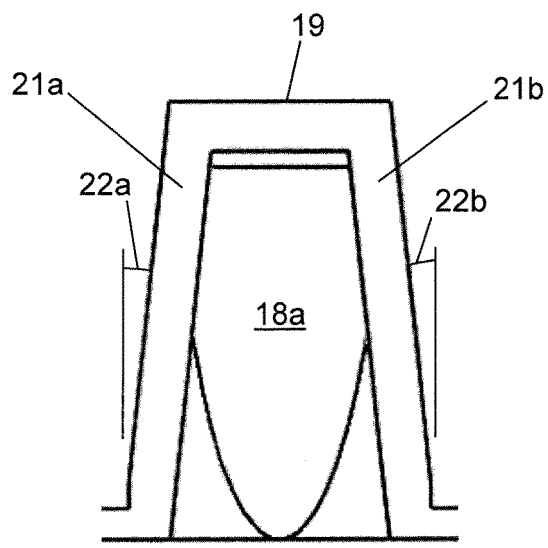
FIG. 4 is a cross sectional view of one embodiment of a one-way air valve, showing the second pair of opposing sidewalls in cross section.

Referring to FIGS. 2-4, the drainage tube assembly 5 comprises a drainage tube 10 with an atmospheric equilibrium valve assembly 11 disposed exterior to the drainage tube 10. The atmospheric equilibrium valve assembly 11 comprises an airway conduit 12 having an upper portion 13 and a lower portion 14, the upper portion 13 disposed in fluid communication with the drainage tube 10, and a lower portion 14 having an air inlet chamber 15 that is disposed in direct fluid communication with the ambient air external to the drainage tube assembly 5. In the embodiment shown in FIG. 2, the airway conduit 12 is disposed parallel, or substantially parallel, to the drainage tube 10. Generally referring again to FIGS. 1-4, a one-way air valve 16 is disposed in the airway conduit 12 above the air inlet chamber 15. The one-way air valve 16 comprises a first pair of opposing walls 17a, 17b disposed at a first set of opposing angles 18a, 18b such that the first pair of opposing walls 17a, 17b abut each other at an apex 19. The first set of opposing angles 18a, 18b comprise two angles 18a, 18b that are approximately equal in degrees (or radians), and opposite in direction so that the respective walls 17a, 17b lean toward each other.

The apex 19 comprises a self-sealing slit 20 defined by the top edge of each wall of the first pair of opposing walls 17a, 17b placed in abutting contact. It is preferred, but not required, that each angle 18a, 18b of the first set of opposing angles 18a, 18b is in the range of about 23° to about 25° when measured in a plane approximately perpendicular to the self-sealing slit 20.

It is preferred, but not required, that the one-way air valve 16 further comprises a second pair of opposing walls 21a, 21b disposed at a second set of opposing angles 22a, 22b. Each wall of the second pair of opposing walls 21a, 21b spans between the first pair of opposing walls 17a, 17b. It is preferred, but not required, that each angle in the second set of opposing angles 22a, 22b is in the range of about 11° to about 13° as measured in a plane approximately parallel to the self-sealing slit 20.

Figure 5:
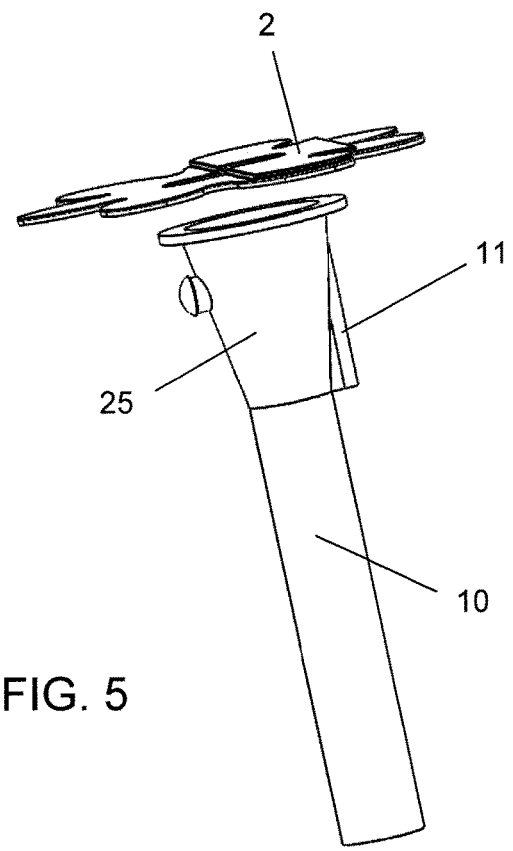
FIG. 5 is an isometric view of one embodiment of the drainage tube assembly position for placement against the parameatal barrier body of a typical external incontinence device.
Figure 6:
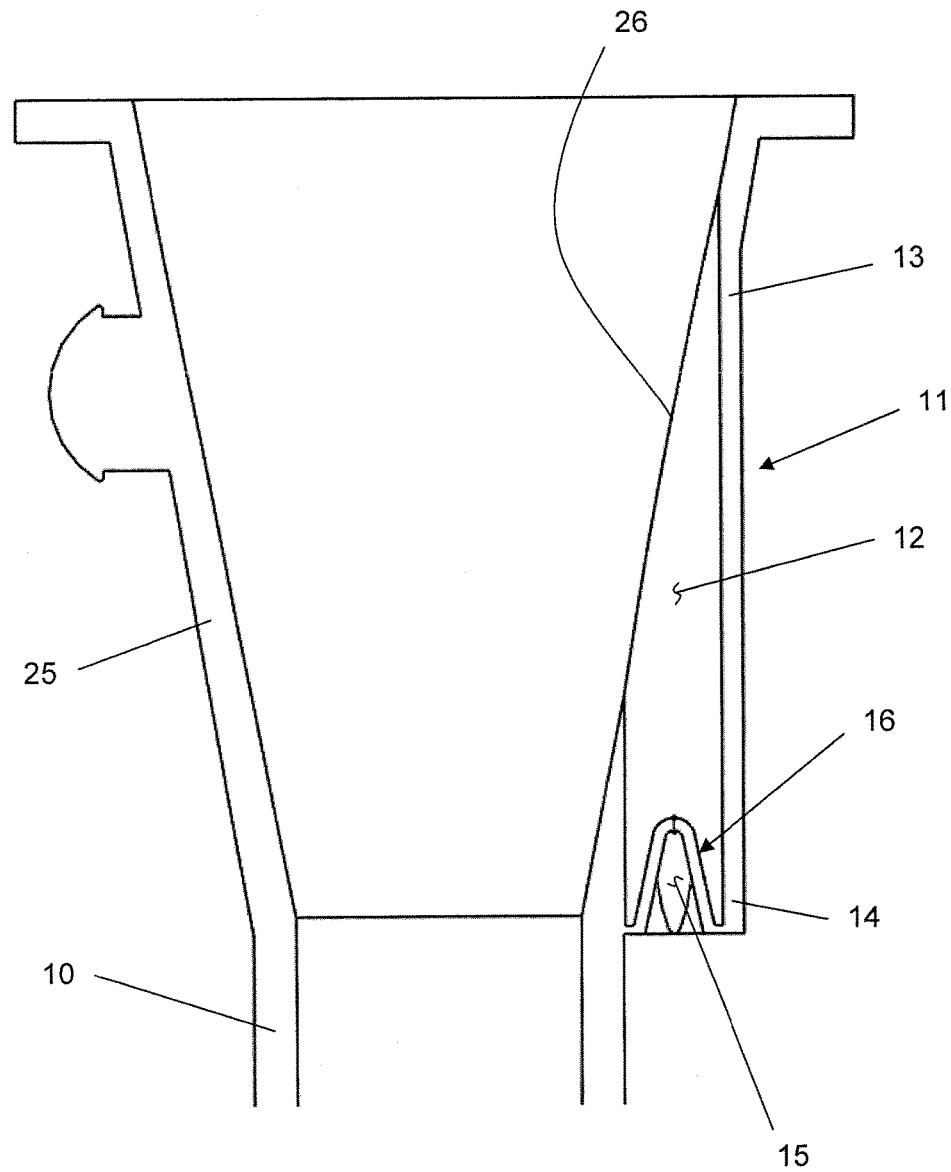
FIG. 6 is a partial cross sectional view of one embodiment of the atmospheric equilibrium valve assembly, where the drainage tube assembly comprises a proximal chamber.
Figure 7:
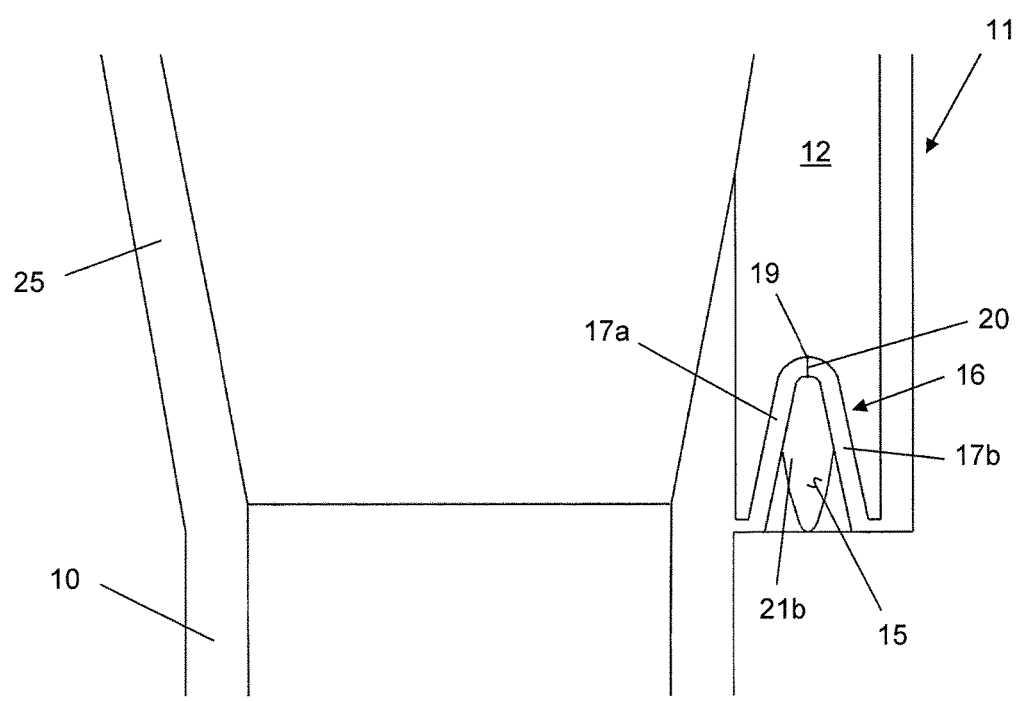
FIG. 7 is an enlarged cross sectional view of the atmospheric equilibrium valve assembly shown in FIG. 6.
Figure 8:
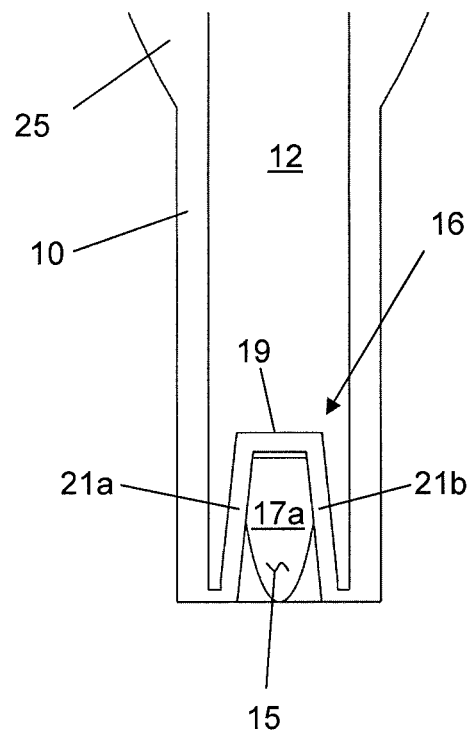
FIG. 8 is an enlarged cross sectional view of the atmospheric equilibrium valve assembly shown in FIG. 7, the view of FIG. 8 being in an orientation perpendicular to the view shown in FIG. 7.
Figure 9:
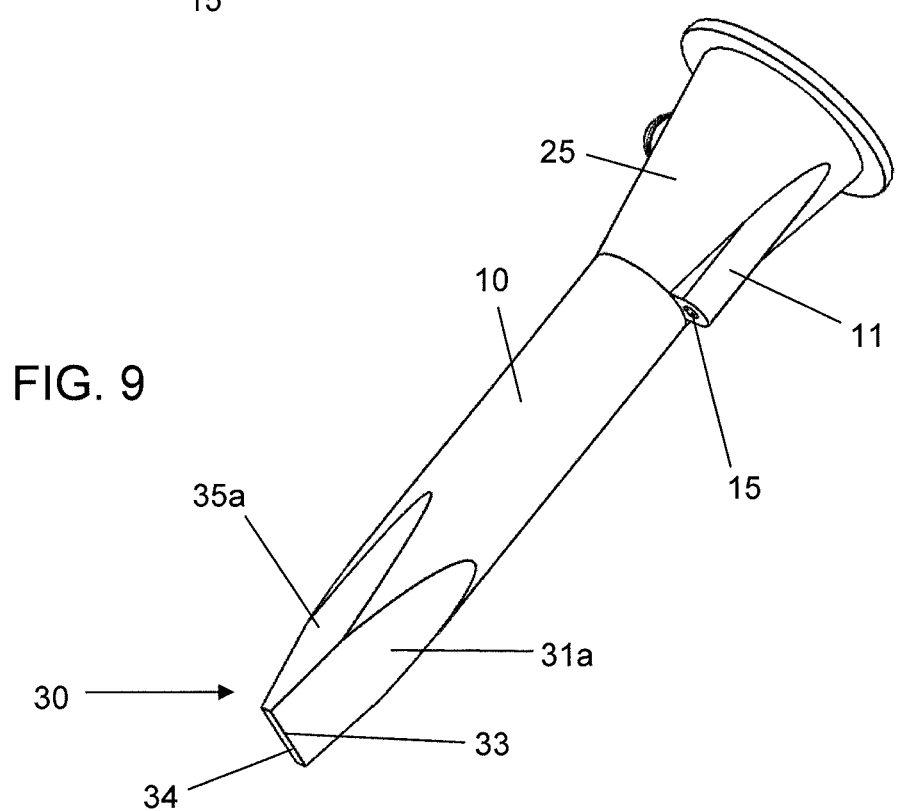
FIG. 9 is an isometric view of one embodiment of the drainage tube assembly having a proximal chamber and an anti-reflux valve.
Figure 10:
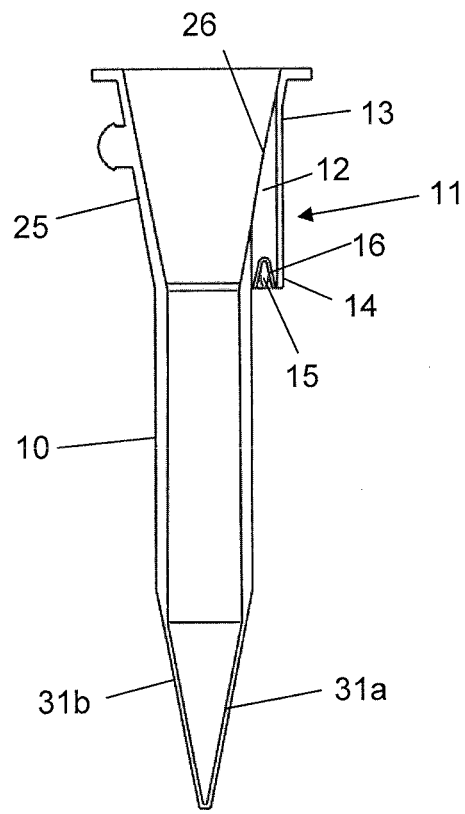
FIG. 10 is a cross section view of the drainage tube assembly shown in FIG. 9.
Figure 11:
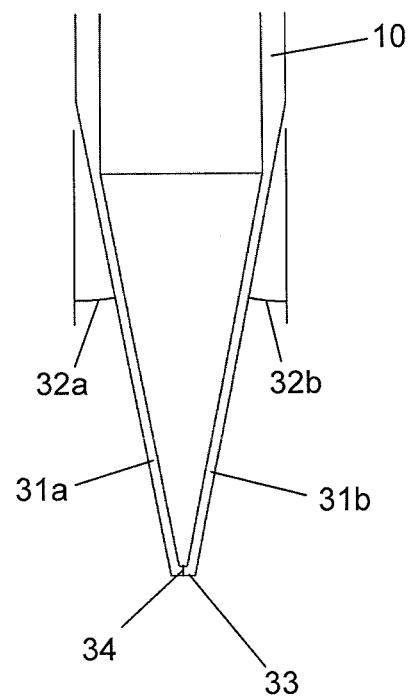
FIG. 11 is an enlarged cross section of the anti-reflux valve shown in FIG. 10.
Figure 12:
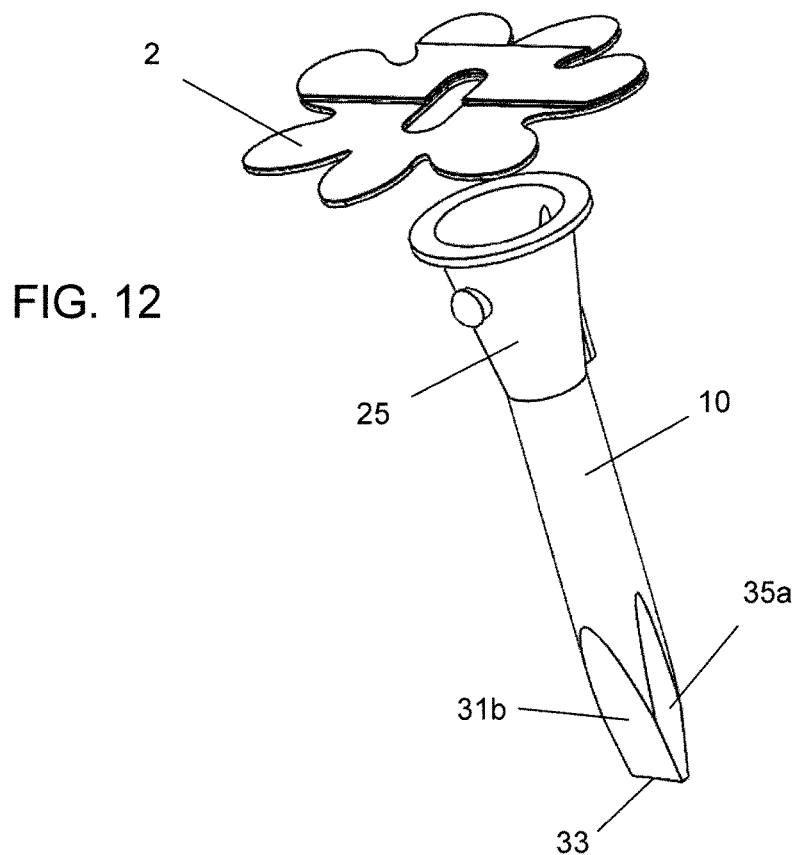
FIG. 12 is an isometric view of the drainage tube assembly shown in FIG. 9 where the drainage tube assembly is position for placement against the parameatal barrier body.
Figure 13:
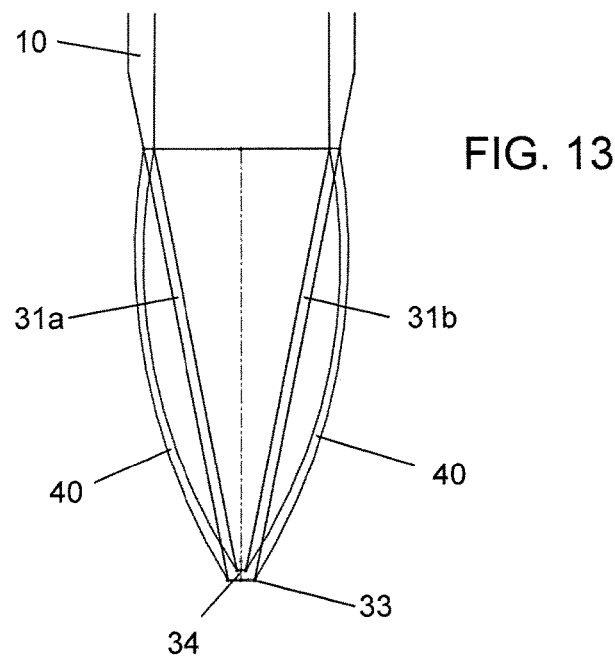
FIG. 13 is an enlarged cross section of the anti-reflux valve shown in FIG. 11, further showing the enlargement of the first pair of anti-reflux walls in a position forming a bellows.

In another embodiment, shown in FIGS. 5-8, the drainage tube assembly 5 further comprises a proximal chamber 25 in fluid communication with a drainage tube 10, the proximal chamber 25 having a frustoconical shape (see, e.g., FIGS. 5 and 6). In this embodiment, the upper portion 13 of the atmospheric equilibrium valve assembly 11, which is disposed on the exterior of the proximal chamber 25, is placed in fluid communication with the proximal chamber 25. More specifically, the airway conduit 12 is disposed in fluid communication with the proximal chamber 25 via an interface 26 having a beveled orientation in relation to the airway conduit 12. The airway conduit 12 is disposed parallel, or substantially parallel, to the drainage tube 10. In this embodiment, the atmospheric equilibrium valve assembly 11 comprises the same elements and embodiments as those disclosed in relation to the drainage tube assembly 5 discussed above.

In any of the foregoing embodiments of the drainage tube assembly 5, it is preferred, but not required, that the atmospheric equilibrium valve assembly 11, and specifically the one-way air valve 16, comprises material that is about 65 Shore A durometer material. Materials suitable for the one-way air valve 16 are a variety of amorphous materials, which often involve sheared material interfaces having behavior described by more complicated constitutive equations than simple fluids or crystalline solids. Amorphous materials flow like a fluid under large stress or creep, or remain stationary under smaller stresses. These materials have complex, history-dependent behavior. Amorphous materials may be subject to changes of their modulus of elasticity, E, by as much as 1,000 times when subjected to small temperature changes that come in direct contact with the material. Amorphous solids are isotropic in nature, which means that in all the directions their physical properties will remain same. Viscoelasticity of the amorphous material allows the material to exhibit both viscous and elastic characteristics when undergoing deformation. Suitable materials for the present atmospheric equilibrium valve assembly 11 will exhibit properties such as high wear resistance, damage tolerance, a Glass Transition ($T_g$) of about +28, moulded tensile strength of about 40 to about 60 $N/m^2$, and a moulded elongation at break of about 425%. One such suitable material is non-phthalate amorphous PVC.

It is preferred, but not required, that the thickness each of the walls of the one-way air valve 16 is about 0.010 inch to about 0.020 inch. In other words, this is the preferred thickness range for each of the walls of the first pair of opposing walls 17a, 17b and the second pair of opposing sidewalls 21a, 21b.

The minimum pressure to open the one-way air valve 16 is about 761 to about 770 mm Hg (about 14.715 to about 14.889 psi). Thus, a small increase in the atmospheric pressure exerting on the inside of the one-way air valve 16 will cause the self-sealing slit 20 to separate, thereby enabling the pressure differential that may be present inside the air inlet chamber 15 to equalize. This equalization will force urine accumulated in the drainage tube 10 through the drainage tube 10 while minimizing or eliminating the siphoning effect. The minimum of pressure to close the one-way air valve 16 is roughly the same as the pressure to open the one-way air valve 16. The viscoelasticity memory properties of the amorphous material assist in the closure of the one-way air valve 16.

The one-way air valve 16 operates and functions on the principle of a pressure differential that may exist in the drainage tube 10, and especially in the proximal chamber 25, and the normal outside atmospheric pressure. For example, as the pressure decreases in the proximal chamber 25 (vacuum created), this will enable air from the outside to open the one-way air valve 16, thereby allowing the proximal chamber 25 to equalize and break any vacuum that may exist in the proximal chamber 25. Applying the barometric formula for this feature would lead to, $dP/dH=-mg/kT \cdot P$, where m=mass of one molecule, h=height of column, g=force of gravity, k=Boltzmann's constant, T=temperature, and P=pressure.

In the unlikely event that liquid enters the airway conduit 12, the angled orientation of the first pair of opposing walls 17a, 17b enables the hydrostatic back pressure against the walls to properly close the self-sealing slit 20, thereby closing the one-way air valve 16. Thus, the one-way action of the valve 16 enables the inflow of air to promote pressure equilibrium, while preventing the backflow of liquid, which would otherwise result in urine leakage from the drainage tube assembly 5.

In another embodiment, shown in FIGS. 9-13, the drainage tube assembly 5 further comprises a self-sealing, anti-reflux valve 30, which preferably comprises the same material as that used for the atmospheric equalization valve assembly 11. Similarly to the one-way air valve 16, the anti-reflux valve 30 comprises a one-way duckbill valve having a first pair of anti-reflux walls 31a, 31b disposed at a third set of opposing angles 32a, 32b to form an anti-reflux apex 33 having a self-sealing anti-reflux slit 34. It is preferable that the anti-reflux valve 30 further comprise a second pair of anti-reflux walls 35a, 35b, which are analogous to the second pair of opposing walls of the one-way air valve 16. The walls in the second pair of anti-reflux walls 35a, 35b are disposed at a fourth set of opposing angles.

It is preferable, but not required, that each of the walls in the anti-reflux valve 30 has a thickness in the range of about 0.015 inch to about 0.025 inch. A thinner wall thickness does not provide sufficient stiffness to force urine through the anti-reflux slit 34, while a thicker wall thickness will not allow anti-reflux valve 30 to form a bellows 40 (see FIG. 13)—the walls 31a, 31b, 35a, 35b would be too stiff and thus may hinder the self-sealing properties of the amorphous polymer material.

Preferably, each angle in the third set of opposing angles 32a, 32b is in the range of about 21 degrees to about 23 degrees as measured in a first plane that is approximately perpendicular to the orientation of the anti-reflux slit 34. Preferably, each angle in the fourth set of opposing angles is in the range of about 3 degrees to about 5 degrees in a second plane that is approximately perpendicular to the first plane, as measured to vertical. Each angle in the third set of opposing angles 32a, 32b and the fourth set of opposing angles can be adjusted to increase the surface area that can be affected by the pressure against the walls 31a, 31b, 35a, 35b, which would increase urine contact and thus the bellows 40 would be larger. This may assist in the complete draining of the drainage tube assembly 5 of fluid. Additionally the larger surface area would be advantageous to allow back pressure against the flat surfaces of the walls 31a, 31b, 35a, 35b thus increasing the self-sealing properties of the anti-reflux valve 30, thereby ensuring the anti-regurgitation feature of the valve 30 is enhanced. The smaller surface area would have the reverse effect.

The minimum pressure to open the anti-reflux valve 30 with urine passing through the drainage tube 10 and contacting the walls 31a, 31b, 35a, 35b is about 14.65 psi (about 758 mm Hg). This pressure could theoretically be smaller as the temperature of the urine will assist in the opening of the anti-reflux valve 30. The minimum of pressure to close the anti-reflux valve 30 is roughly the same as the pressure to open the valve 30, which is about 14.65 psi (about 758 mm Hg). It is preferable, but not required, that the anti-reflux valve comprises the same amorphous material with a 65 Shore A durometer.

The foregoing embodiments are merely representative of the external incontinence device and not meant for limitation of the invention. For example, persons skilled in the art would readily appreciate that there are several embodiments and configurations of the first pair of opposing walls, second pair of opposing walls, and other components of the drainage tube assembly that will not substantially alter the nature of the present external incontinence device. Likewise, elements and features of the disclosed embodiments could be substituted or interchanged with elements and features of other embodiments, as will be appreciated by an ordinary practitioner. Consequently, it is understood that equivalents and substitutions for certain elements and components set forth above are part of the invention described herein, and the true scope of the invention is set forth in the claims below.

The invention claimed is:

1. A drainage tube assembly for an external incontinence device, the drainage tube assembly comprising:
    a drainage tube with an atmospheric equilibrium valve assembly disposed exterior to the drainage tube, the atmospheric equilibrium valve assembly comprising:
        an airway conduit disposed substantially parallel to the drainage tube, the airway conduit having an upper portion in fluid communication with the drainage tube, and a lower portion having an air inlet chamber disposed in direct fluid communication with air external to the drainage tube assembly; and
        a one-way air valve disposed in the airway conduit above the air inlet chamber, the one-way air valve comprising a first pair of opposing walls disposed at a first set of opposing angles such that the first pair of opposing walls abut each other at a first apex, the first apex having a self-sealing slit.

2. The assembly of claim 1, wherein the first pair of opposing walls comprise material having a durometer of about 65 Shore A, and each wall of the first pair of opposing walls has a thickness that ranges from about 0.010 inches to about 0.020 inches.

3. The assembly of claim 2, wherein each angle of the first set of opposing angles is in the range of about 23° to about 25° in a plane approximately perpendicular to the self-sealing slit.

4. The assembly of claim 3, further comprising a second pair of opposing walls, the second pair of opposing walls disposed at a second set of opposing angles, each angle of the second set of opposing angles being in the range of about 11° to about 13° in a plane approximately parallel to the self-sealing slit.

5. The assembly of claim 3, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

6. The assembly of claim 1, wherein each angle of the first set of opposing angles is in the range of about 23° to about 25° in a plane approximately perpendicular to the self-sealing slit.

7. The assembly of claim 6, further comprising a second pair of opposing walls, the second pair of opposing walls disposed at a second set of opposing angles, each angle of the second set of opposing angles being in the range of about 11° to about 13° in a plane approximately parallel to the self-sealing slit.

8. The assembly of claim 7, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

9. The assembly of claim 1, further comprising a second pair of opposing walls, the second pair of opposing walls disposed at a second set of opposing angles, each angle of the second set of opposing angles being in the range of about 11° to about 13° in a plane approximately parallel to the self-sealing slit.

10. The assembly of claim 1, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

11. A drainage tube assembly for an external incontinence device, the drainage tube assembly comprising:
   a proximal chamber in fluid communication with a drainage tube, the proximal chamber having a frustoconical shape and comprising an atmospheric equilibrium valve assembly disposed exterior to the proximal chamber, the atmospheric equilibrium valve assembly comprising:
       an airway conduit disposed substantially parallel to the drainage tube, the airway conduit having an upper portion in fluid communication with the proximal chamber via an interface having a beveled orientation in relation to the airway conduit, and a lower portion having an air inlet chamber disposed in direct fluid communication with air external to the drainage tube assembly; and
       a one-way air valve disposed in the airway conduit above the air inlet chamber, the one-way air valve comprising a first pair of opposing walls disposed at a first set of opposing angles such that the first pair of opposing walls abut each other at a first apex, the first apex having a self-sealing slit.

12. The assembly of claim 11, wherein the first pair of opposing walls comprise material having a durometer of about 65 Shore A, and each wall of the first pair of opposing walls has a thickness that ranges from about 0.010 inches to about 0.020 inches.

13. The assembly of claim 12, wherein each angle of the first set of opposing angles is in the range of about 23° to about 25° in a plane approximately perpendicular to the self-sealing slit.

14. The assembly of claim 13, further comprising a second pair of opposing walls, the second pair of opposing walls disposed at a second set of opposing angles, each angle of the second set of opposing angles being in the range of about 11° to about 13° in a plane approximately parallel to the self-sealing slit.

15. The assembly of claim 13, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

16. The assembly of claim 11, wherein each angle of the first set of opposing angles is in the range of about 23° to about 25° in a plane approximately perpendicular to the self-sealing slit.

17. The assembly of claim 16, further comprising a second pair of opposing walls, the second pair of opposing walls disposed at a second set of opposing angles, each angle of the second set of opposing angles being in the range of about 11° to about 13° in a plane approximately parallel to the self-sealing slit.

18. The assembly of claim 17, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

19. The assembly of claim 11, further comprising a second pair of opposing walls, the second pair of opposing walls disposed at a second set of opposing angles, each angle of the second set of opposing angles being in the range of about 11° to about 13° in a plane approximately parallel to the self-sealing slit.

20. The assembly of claim 11, further comprising an anti-reflux valve disposed at the bottom of the drainage tube, the anti-reflux valve comprising a first pair of anti-reflux walls disposed at a third set of opposing angles, each angle of the third set of opposing angles being in the range of about 21° to about 23°, such that the first pair of anti-reflux walls abut each other at a second apex, the second apex having a self-sealing anti-reflux slit.

* * * * *